US011519911B2

(12) United States Patent
Levy et al.

(10) Patent No.: US 11,519,911 B2
(45) Date of Patent: Dec. 6, 2022

(54) ALX RECEPTOR LIGANDS DEFINE A BIOCHEMICAL ENDOTYPE FOR INFLAMMATION-BASED DISEASES

(71) Applicant: THE BRIGHAM AND WOMEN'S HOSPITAL, INC., Boston, MA (US)

(72) Inventors: Bruce Levy, West Roxbury, MA (US); Charles N. Serhan, Needham, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 300 days.

(21) Appl. No.: 16/482,216

(22) PCT Filed: Jan. 25, 2018

(86) PCT No.: PCT/US2018/015287
§ 371 (c)(1),
(2) Date: Jul. 30, 2019

(87) PCT Pub. No.: WO2018/144316
PCT Pub. Date: Aug. 9, 2018

(65) Prior Publication Data
US 2019/0391145 A1 Dec. 26, 2019

Related U.S. Application Data

(60) Provisional application No. 62/452,533, filed on Jan. 31, 2017.

(51) Int. Cl.
*G01N 33/566* (2006.01)

(52) U.S. Cl.
CPC ....... *G01N 33/566* (2013.01); *G01N 2800/12* (2013.01); *G01N 2800/122* (2013.01);
(Continued)

(58) Field of Classification Search
CPC ............ G01N 33/566; G01N 2800/12; G01N 2800/122; G01N 2800/127;
(Continued)

(56) References Cited

U.S. PATENT DOCUMENTS 6,831,186 B2    12/2004   Bauman
7,615,576 B2    11/2009   Serhan
(Continued)

FOREIGN PATENT DOCUMENTS

EP       1911448 A2    4/2008
WO    2000054767 A     9/2000
(Continued)

OTHER PUBLICATIONS

Back (British J. Pharmacology 2014 vol. 171: 3551-3574) (Year: 2014).*
(Continued)

*Primary Examiner* — Changhwa J Cheu
(74) *Attorney, Agent, or Firm* — Haukaas Fortius PLLC; Colin L. Fairman

(57) ABSTRACT

A method to determine the severity of a disease of chronic inflammation in a patient, comprising the steps of (1) collection or preparation of a bodily fluid, tissue or lavage and (2) measurement of ALX receptor ligands or ALX receptor expression in the fluid, tissue, or lavage, wherein the level of ALX receptor ligands predicts a clinical outcome or choice of treatment modality, is disclosed.

5 Claims, 6 Drawing Sheets

(52) U.S. Cl.
CPC . *G01N 2800/127* (2013.01); *G01N 2800/245* (2013.01); *G01N 2800/382* (2013.01); *G01N 2800/50* (2013.01); *G01N 2800/56* (2013.01)

(58) Field of Classification Search
CPC ....... G01N 2800/245; G01N 2800/382; G01N 2800/50; G01N 2800/56
See application file for complete search history.

(56) References Cited

U.S. PATENT DOCUMENTS

| | | | |
|---|---|---|---|
| 7,700,650 | B2 | 4/2010 | Van Dyke |
| 7,906,678 | B2 | 3/2011 | Haag |
| 2019/0033322 | A1* | 1/2019 | Li .......................... A61P 11/06 |

FOREIGN PATENT DOCUMENTS

| | | |
|---|---|---|
| WO | 2002070068 A2 | 9/2002 |
| WO | 2003039533 A1 | 5/2003 |
| WO | 2016185385 A1 | 11/2016 |

OTHER PUBLICATIONS

Yarur et al. (Inflammation Bowel Disease 2017 vol. 23: 158-164) (Year: 2017).*
Celik (Clin. Exp. Allergy 2007 vol. 37: 1494-1501). (Year: 2007).*
Gagliardo (J. Allergy Clin. Immunol. 2016 137:1796-806) (Year: 2016).*
Kazani S. et al., "Exhaled Breath Condensate Eicosanoid Levels Associate with Asthma and its severity", J Allergy Clin Immunol (Sep. 2013).
Levy B. et al., "Resolvin D1 and Resolvin E1 Promote the Resolution of Allergic Airway Inflammation Via Shared and Distinct Molecular Counter-Regulatory Pathways", Frontiers in Immunology, vol. 3 (Dec. 2012).
Vachier I. et al., "Severe Asthma is Associated with a Loss of LX4, an Endogenous Anti-Inflammatory Compound", J Allergy Clin Immunol (Jan. 2005).
Ariel A, et al. Aspirin-triggered lipoxin A4 and B4 analogs block extracellular signal-regulated kinase-dependent TNF-alpha secretion from human T cells. J Immunol. 2003;170(12):6266-72.
Bena S, et al. Annexin A1 interaction with the FPR2/ALX receptor: identification of distinct domains and downstream associated signaling. The Journal of biological chemistry. 2012;287(29):24690-7.
Bozinovski, S., et al. "Serum amyloid A opposes lipoxin A4 to mediate glucocorticoid refractory lung inflammation in chronic obstructive pulmonary disease." Proceedings of the National Academy of Sciences 109.3 (2012): 935-940.
Chiang N, et al. Activation of lipoxin A(4) receptors by aspirin-triggered lipoxins and select peptides evokes ligand-specific responses in inflammation. The Journal of experimental medicine. 2000;191(7):1197-208.
Chiang, N., et al. "Aspirin-triggered 15-epi-lipoxin A4 (ATL) generation by human leukocytes and murine peritonitis exudates: development of a specific 15-epi-LXA4 ELISA." Journal of Pharmacology and Experimental Therapeutics 287.2 (1998): 779-790.
Chiang, N., et al. "The lipoxin receptor ALX: potent ligand-specific and stereoselective actions in vivo." Pharmacological reviews 58.3 (2006): 463-487.
El Kebir, D., et al. "15-epi-lipoxin A4 inhibits myeloperoxidase signaling and enhances resolution of acute lung injury." American journal of respiratory and critical care medicine 180.4 (2009): 311-319.
El Kebir, D., et al. "Aspirin-triggered lipoxins override the apoptosis-delaying action of serum amyloid A in human neutrophils: a novel mechanism for resolution of inflammation." The Journal of Immunology 179.1 (2007): 616-622.
Gronert K, et al. Selectivity of recombinant human leukotriene D(4), leukotriene B(4), and lipoxin A(4) receptors with aspirin-triggered 15-epi-LXA(4) and regulation of vascular and inflammatory responses. The American journal of pathology. 2001;158(1):3-9.
International Searching Authority, International Search Report and Written Opinion for application PCT/US2018/015287, dated Mar. 26, 2018.
Ledford, D. K., et al. "Asthma and comorbidities." Current opinion in allergy and clinical immunology 13.1 (2013):78-86.
Maderna P, et al. FPR2/ALX receptor expression and internalization are critical for lipoxin A4 and annexin-derived peptide-stimulated phagocytosis. FASEB journal : official publication of the Federation of American Societies for Experimental Biology. 2010;24(11):4240-9.
Planaguma, A., et al. "Airway lipoxin A4 generation and lipoxin A4 receptor expression are decreased in severe asthma." American journal of respiratory and critical care medicine 178.6 (2008): 574-582.
Ricklefs, I., et al. "ALX receptor ligands define a biochemical endotype for severe asthma." JCI insight 2.14 (2017).
Serhan, C. N., et al. "The resolution code of acute inflammation: novel pro-resolving lipid mediators in resolution." Seminars in immunology. vol. 27. No. 3. Academic Press, 2015.
Sodin-Semrl, S., et al. "Lipoxin A4 and Serum Amyloid a Differentially Modulate Phospholipase D in Human Fibroblast-Like Synoviocytes." European Journal of Inflammation 7.1 (2009): 9-17.
Wu SH, et al. Efficacy and safety of 15(R/S)-methyl-lipoxin A(4) in topical treatment of infantile eczema. Br J Dermatol. 2013;168(1):172-8.
Xiong et al. "The relationship between serum amyloid A and acute exacerbation of chronic obstructive pulmonary disease and its clincal significane", Jiangxi Medical Journal, May 20, 2009, vol. 44, No. 5, pp. 420-422.

* cited by examiner

FIG. 1A-E

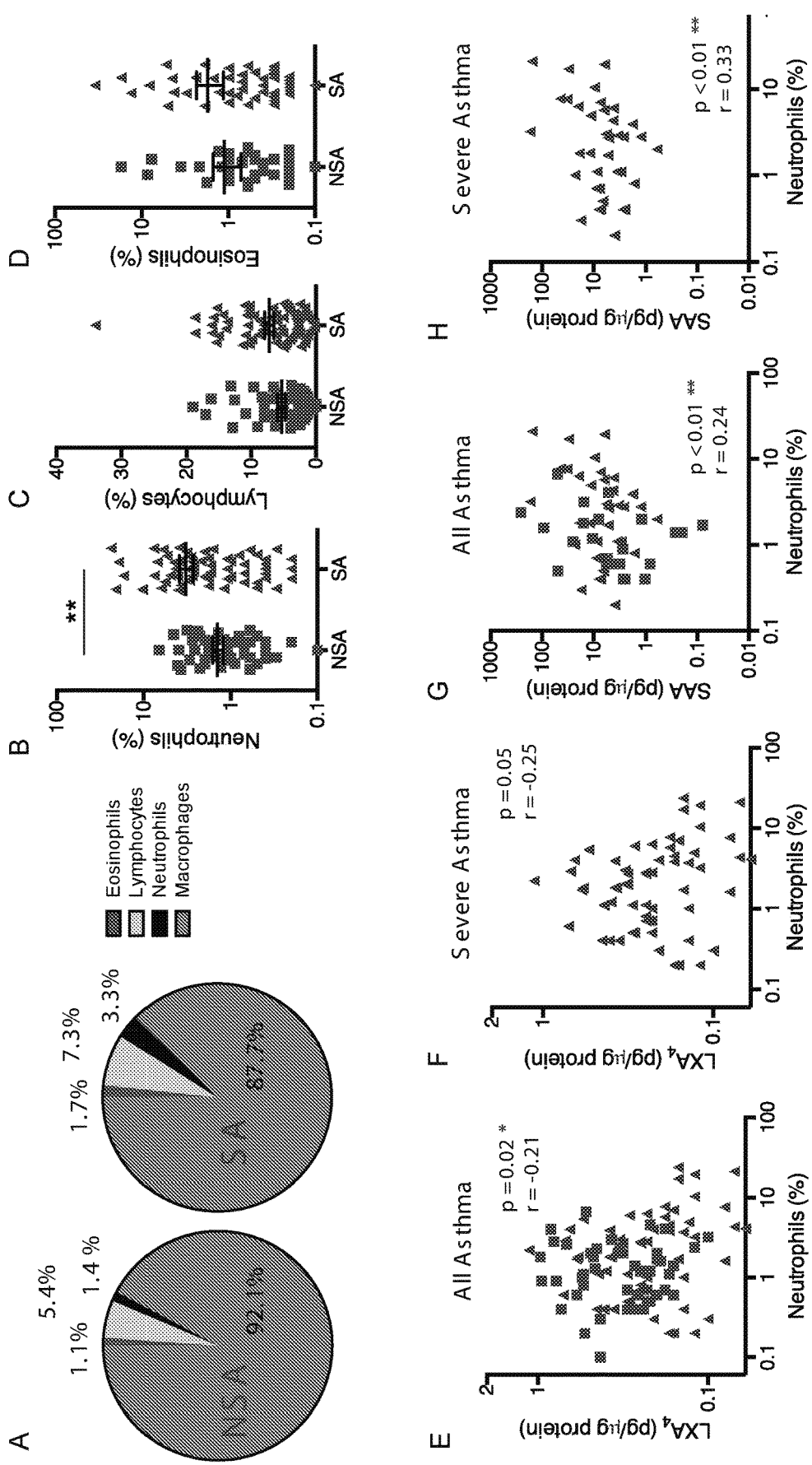
FIG. 3A-H

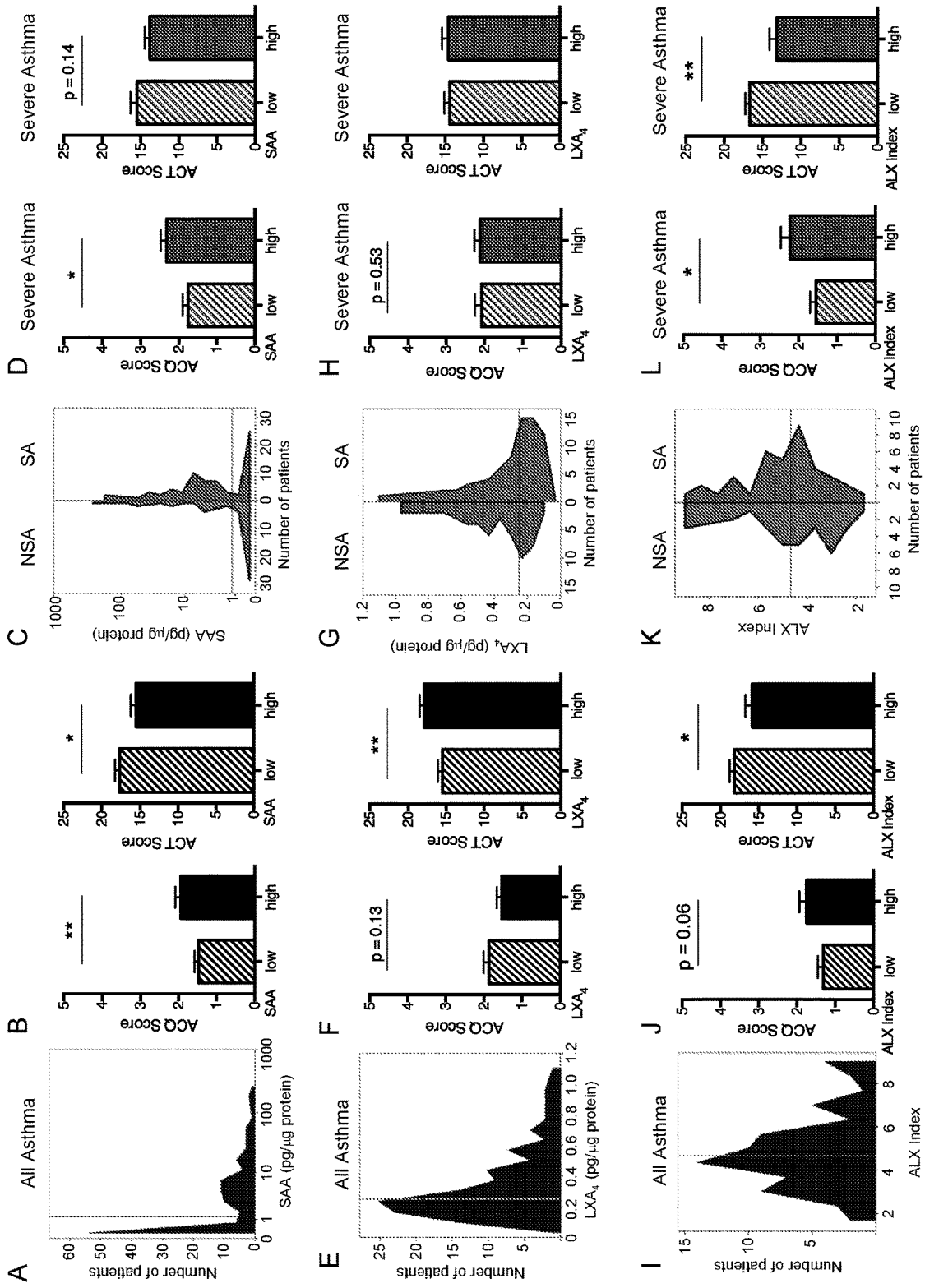
FIG. 4A-L

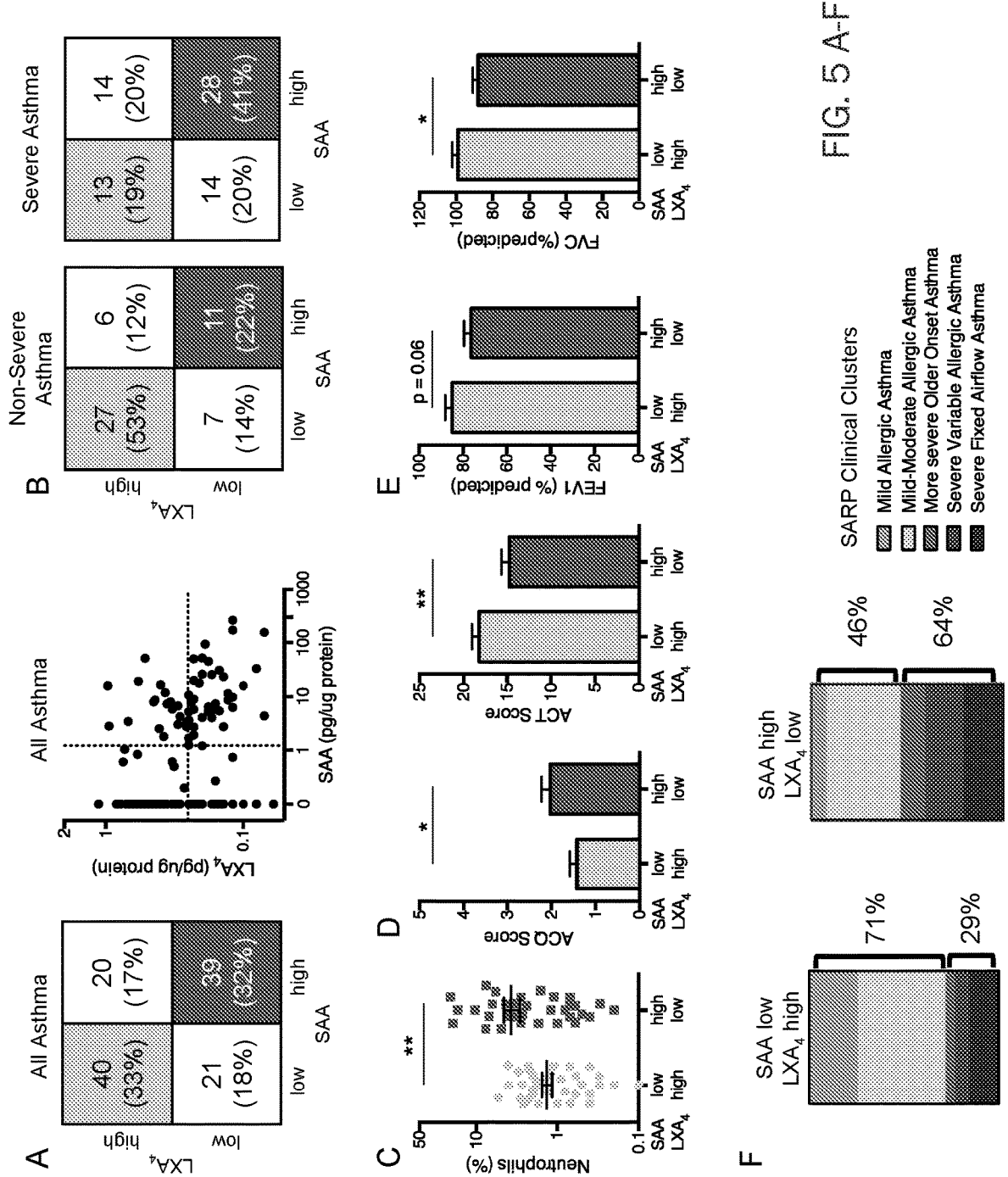
FIG. 5 A-F

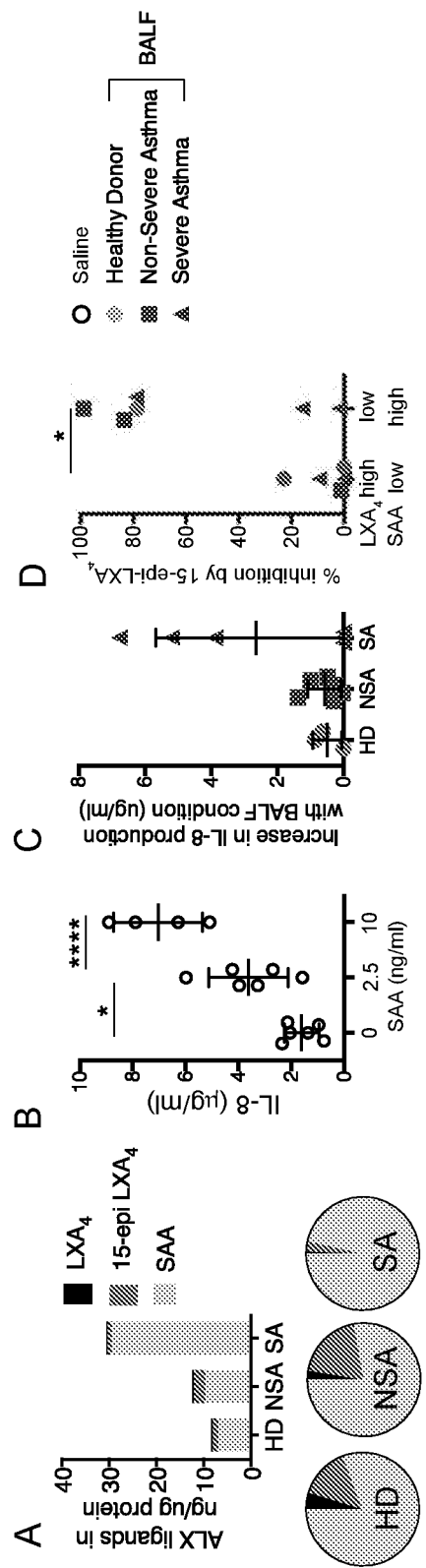
FIG. 6A-D

ALX RECEPTOR LIGANDS DEFINE A BIOCHEMICAL ENDOTYPE FOR INFLAMMATION-BASED DISEASES

CROSS-REFERENCE TO RELATED APPLICATIONS

This application represents the national stage entry of international application PCT/US2018/015287, filed Jan. 25, 2018, which claims benefit of U.S. Provisional Application 62/452,533 filed Jan. 31, 2017. All of which are incorporated herein by reference for all purposes.

STATEMENT REGARDING FEDERALLY SPONSORED RESEARCH

This invention was made with government support under HL109172 awarded by the National Institutes of Health. The government has certain rights in the invention.

BACKGROUND

Asthma is the most common disease of chronic lung inflammation, affecting nearly 1 in 13 Americans (1). The current clinical criteria for the diagnosis of asthma include a broad spectrum of patients with heterogeneous disease processes and distinct responses to medications (2). Approximately 10-15% of asthmatic patients have severe asthma (SA) with daily symptoms and inadequate asthma control despite asthma-targeted controller medication use. These patients with SA have increased morbidity with significant adverse outcomes, including frequent outpatient visits, admissions to the hospital, and even life threatening exacerbations (3). Cluster analyses utilizing patient clinical characteristics have identified at least 5 distinct clusters of asthmatic individuals (4, 5). Identifying disease mechanisms in asthma pathogenesis is critical to move the field from clinical phenotyping to molecular endotyping of patients to enable precision medicine approaches for improved asthma management (6). While Type 2 "high" inflammation accounts for approximately 50% of asthma pathobiology (7), disease mechanisms for the remaining 50% of asthmatic subjects remain to be determined. A more detailed understanding of mechanisms underlying non-Type 2 inflammation in asthma is needed.

In health, the resolution of inflammation is an active process governed by specific cellular events regulated by specialized pro-resolving mediators (SPMs) derived from essential fatty acids (8). $LXA_4$ and 15-epi-$LXA_4$ are endogenous arachidonic acid-derived SPMs that potently regulate acute inflammation, yet are under-produced in many inflammatory diseases, including SA (9). Lipoxins and their stable analogs are protective in murine models of allergic lung inflammation, and display cell type-specific actions for human leukocytes to inhibit pro-inflammatory interleukin-13 production by group 2 innate lymphoid cells, halt granulocyte trafficking and activation, decrease T cell cytokine production, enhance natural killer cell functions and stimulate macrophage CD206 expression and efferocytosis to resolve tissue inflammation (Reviewed in (9)). Lipoxins also inhibit leukotriene mediated pro-phlogistic actions, including in vivo in asthma (10), and decrease cytokine-induced human airway contractile responses (11). In peripheral blood, exhaled breath condensates, sputum, and BALF, $LXA_4$ levels are decreased in SA relative to non-severe asthma (NSA) (12-15), suggesting a link between defective resolution mechanisms and persistent airway inflammation in some asthma patients.

$LXA_4$ and 15-epi-$LXA_4$ interact with specific receptors to exert their pro-resolving actions. Their high affinity cognate receptors are ALX/$FPR_2$ receptors (ALX) with a KD of approximately 1 nM (16). Of interest, ALX was the first receptor described to engage both lipid and peptide ligands (16) and subsequently several lipid and peptide ligands for ALX have been identified. Ligand recognition sites differ in the extracellular domains of ALX receptors and trigger distinct downstream events that dramatically change the signaling properties of the receptor depending on the engaging ligand (17). In sharp contrast to $LXA_4$'s counter-regulatory signaling, SAA engages the same ALX receptors to promote inflammation (18, 19). SAA is generated as an acute phase protein in COPD exacerbations in amounts that are 2-3 log orders higher than $LXA_4$ that overwhelms SPM signaling via ALX (18). Another ALX ligand of potential interest in severe asthma is annexin A1 (ANXA1), a corticosteroid-inducible protein that can interact with ALX receptors to transduce pro-resolving actions similar to $LXA_4$ (20). Of interest, when apparently healthy individuals are challenged with a skin irritant, they segregate into fast and slow resolvers of the dermal wound based on lipoxin production and expression of ALX receptors (21). Thus, relative levels of these lipid and peptide ALX ligands could serve as a rheostat for inflammatory host responses in airway disease, as lipoxins can allosterically inhibit SAA interactions with ALX (18). Together, the relative abundance and actions of these pro-inflammatory versus pro-resolving ALX ligands may biochemically regulate airway phlogistic tone and contribute to unresolved inflammation in SA.

In the Examples below, we analyzed BALF samples collected from subjects participating in NHLBI SARP—3 and have identified a new asthma biochemical endotype related to levels of the ALX receptor ligands $LXA_4$ and SAA that was associated with neutrophilic inflammation, increased asthma symptoms and decreased lung function in SA. This endotype will be useful in diagnosis and treatment of other inflammation-based diseases.

SUMMARY OF THE INVENTION

In one embodiment, the present invention is a method to determine the severity of a disease of chronic inflammation in a patient comprising the steps of (a) collection or preparation of a bodily fluid, tissue or lavage, and (b) measurement of ALX receptor ligands or ALX receptor expression in the fluid, tissue, or lavage, wherein the level of ALX receptor ligands predicts a clinical outcome or choice of treatment modality. Preferably, the ALX receptor ligands are selected from the group consisting of $LXA_4$, 15-epi-$LXA_4$ and SAA. In some embodiments, the measurement results in a ratio.

In one embodiment of the invention, the disease of chronic inflammation is selected from the group consisting of pathologic lung inflammation, arthritis, inflammatory bowel disease atherosclerosis and psoriasis. In some embodiments, the disease of lung inflammation is cystic fibrosis or asthma. In other embodiments, the disease of lung inflammation is selected from the group consisting of COPD, bronchiectasis, bronchiolitis, interstitial lung disease, transplant rejection, pneumonitis, lung abscess, pulmonary vascular disease, pulmonary emboli, and ARDS. In some embodiments the levels of lipoxin$A_4$ and serum amyloid A are measured and the ratio predicts a severe disease clinical outcome including increased lung inflammation, increased asthma symptomology, lower lung function and an increased risk for asthma co-morbidities.

In some embodiments, the fluid or lavage is bronchoalveolar lavage. In some embodiments the fluid, tissue, or lavage is selected from the group consisting of blood, serum, plasma, urine, nasal lavage, sputum, exhaled breath condensate, tears, breast milk, semen, pleural fluid, pericardial fluid, and joint fluid.

In one embodiment of the invention, the expression of the ALX/FPR2 receptor by macrophages in said tissue, fluid, or lavage predicts a severe disease clinical outcome including increased lung inflammation, increased asthma symptomology, lower lung function and an increased risk for asthma co-morbidities.

In one embodiment, the present invention is a method of measuring ALX receptor ligands or ALX receptor expression in a fluid, tissue, or lavage, wherein the method comprises the steps of (a) obtaining a patient tissue, fluid or lavage and (b) determining the amount of ALX receptor ligands or ALX receptor expression in the fluid, tissue, or lavage. In some embodiments, the fluid, tissue, or lavage is broncholalveolar lavage or may be selected from the group consisting of blood, serum, plasma, urine, nasal lavage, sputum, exhaled breath condensate, tears, breast milk, semen, pleural fluid, pericardial fluid, and joint fluid.

DESCRIPTION OF FIGURES

FIG. 3 A-H. BAL neutrophils are increased in severe asthma and differentially related to BALF $LXA_4$ and SAA levels. BAL samples were obtained from NSA and SA subjects and leukocyte subsets were enumerated. (A) Pie charts express the mean percentage of BAL neutrophils, lymphocytes, eosinophils and macrophages in n=47 HD, n=51 NSA, and n=69 SA subjects. (B-D) Scatter plots show individual subject data points with mean±SEM for BAL (B) neutrophils, (C) lymphocytes, and (D) eosinophils in the HD (gray circles), NSA (blue squares), and SA (red triangles) cohorts. **$p<0.01$ by 2-tailed Student's t-test. (E-F) The relationship between BALF neutrophils and $LXA_4$ was determined for (E) all asthma subjects and (F) for the SA cohort only. (G-H) The relationship between BALF neutrophils and SAA was determined for (G) all asthma subjects and (H) for the SA cohort only. SAA levels that were undetectable were assigned a value of 0 pg/μg protein and were included in the correlation analysis. Pearson correlation r-value and significance are noted and regression lines are shown. HD, healthy donors; NSA, non-severe asthma; SA, severe asthma; $LXA_4$, lipoxin $A_4$; SAA, serum amyloid A.

FIG. 4 A-L. SAA and macrophage ALX expression are associated with increased symptoms in severe asthma. Asthma subjects were categorized into subgroups based on "low" or "high" BALF levels of SAA (A-D), $LXA_4$ (E-H) and macrophage ALX expression (I-L). The median value for each variable was used to define the cutoff between the "low" and "high" subgroups (SAA cutoff=1.22 pg/μg protein, $LXA_4$ cutoff=0.25 pg/μg protein, ALX Index cutoff=4.6). Cutoff values are delineated by the grey vertical line. A histogram shows the distribution of subjects based on BALF (A) SAA level, (E) $LXA_4$ level, and (I) BAL macrophage ALX Index. (B, F, J) Validated measures of asthma symptoms (ACQ and ACT scores) were compared between low (open circles) and high (closed circles) subgroups for SAA, $LXA_4$, and ALX index. (C, G, K) The distributions of SAA, $LXA_4$ and ALX index among NSA (blue) and SA (red) subjects are shown in violin plots. (D, H, L) ACQ and ACT scores were compared in SA subjects for low (open triangles) and high (closed triangles) subgroups for SAA, $LXA_4$ and ALX index. Scatter plots show individual subject data with mean±SEM. n=51 NSA and n=69 SA subjects.*$p<0.05$, **$p<0.01$ by Mann-Whitney test or 2-tailed Student's t-test. SAA, serum amyloid A; ACQ, asthma control questionnaire; ACT, asthma control test; NSA, non-severe asthma; SA, severe asthma; $LXA_4$, lipoxin $A_4$; ALX, airway lipoxin $A_4$ receptor.

FIG. 5 A-F. BALF SAA and $LXA_4$ levels are distinct in clinically severe and non-severe asthma. (A) The number and percentages of asthma subjects with BALF levels of $LXA_4$ and SAA that were below ("low") or above ("high") the median value were identified and subjects were grouped into 4 phenotypes based on $LXA_4$ and SAA levels. Noted are subjects in the $LXA_4^{high} SAA^{low}$ group (beige quadrant), and $LXA_4^{low} SAA^{high}$ (purple quadrant). The relationship between individual subject levels of $LXA_4$ and SAA was determined for all asthma subjects. (B) The four groups of subjects based on BALF SAA and $LXA_4$ low and high cohorts were determined for subjects and stratified by asthma severity; NSA (left), SA (right). (C) The relationship between the SAA/$LXA_4$ ratio and BAL neutrophils (%) was determined in n=120 asthma subjects. Pearson correlation r-value and significance are noted and regression line is shown. (D-F) Scatter plots show comparisons of subjects in the $LXA_4^{high}SAA^{low}$ group (beige) to subjects in the $LXA_4^{low}SAA^{high}$ group (purple) for measures of (D) inflammation (BALF neutrophils (%)), (E) asthma symptoms (ACQ, ACT scores) and (F) lung function (% predicted FEV1 and FVC). (G) Subjects in the $LXA_4^{high}SAA^{low}$ and $LXA_4^{low}SAA^{high}$ groups were assigned to clinical clusters as defined in SARP-1 (5) and the percent of subjects assigned to NSA and SA clusters is indicated. n=51 NSA and n=69 SA subjects.*p<0.05, **p<0.01 by 2-tailed Student's t-test. $LXA_4$, lipoxin $A_4$; SAA, serum amyloid A; NSA, non-severe asthma; SA, severe asthma; ACQ, asthma control questionnaire; ACT, asthma control test; FEV1, forced expiratory volume in 1 second; FVC, forced vital capacity; SARP, severe asthma research program.

FIG. 6 A-D. SAA and 15-epi-$LXA_4$ signaling via ALX receptors regulates production of the neutrophil chemoattractant IL-8 A549 human epithelial cells expressing human ALX receptors ($A549^{hALX}$) were exposed to BALF from HD, NSA, or SA subjects (24 h, 37° C., 5% $CO_2$) and IL-8 levels were measured in the cell-free supernatant by ELISA (see Methods). (A) Mean levels of $LXA_4$, 15-epi-$LXA_4$ and SAA in BALF from n=15 subjects used for $A549^{hALX}$ cell incubations are shown in stacked bar graphs and the relative proportions are noted in pie charts. (B) IL-8 production by $A549^{hALX}$ cells was measured after incubation with saline control or SAA (2.5 ng/ml or 10 ng/ml) for 24 hours. (C) IL-8 production by $A549^{hALX}$ cells was measured after 24 hours of exposure to BALF from HD (n=3), NSA (n=6) or SA (n=5) and is expressed as an increase relative to saline controls. Incubations with BALF without an increase in IL-8 production relative to saline control were assigned a value of zero. (D) $A549^{hALX}$ epithelial cells were exposed to BALF from subjects with endogenous levels that were $LXA_4^{high}SAA^{low}$ (n=5) or $LXA_4^{low}SAA^{high}$ (n=6) followed by exposure to exogenous 15-epi-$LXA_4$ (100 nM). % Inhibition of IL-8 production after 15-epi-$LXA_4$ exposure was calculated. *p<0.05, ****p<0.001 by (B) one-way ANOVA (C) Kruskal-Wallis test and (D) Mann-Whitney test. ALX, airway lipoxin $A_4$ receptor; $LXA_4$, lipoxin $A_4$; 15-epi-$LXA_4$, 15-epimer lipoxin $A_4$; SAA, serum amyloid A; HD, healthy donors; NSA, non-severe asthma; SA, severe asthma; IL-8, interleukin-8; BALF, bronchoalveolar lavage fluid.

DETAILED DESCRIPTION OF THE INVENTION

In General

Figure 1:
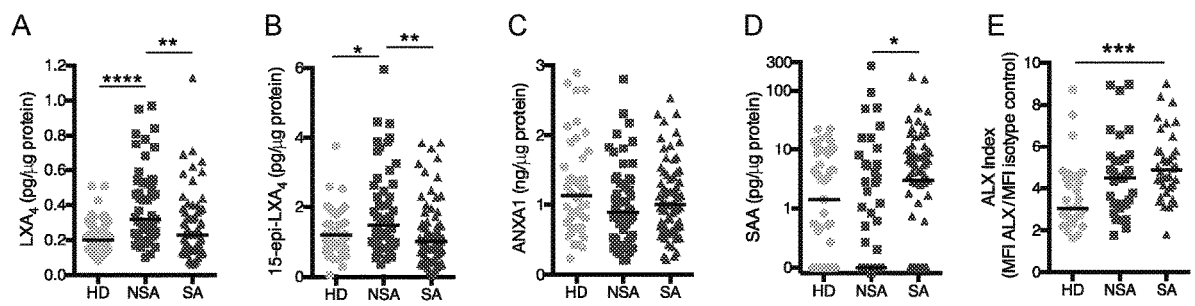
FIG. 1 A-E. Relative abundance of BALF ALX ligands and ALX receptor expression differs in asthma. BALF was obtained from subjects with asthma (n=120) and healthy donors (n=47, grey circles). Asthmatic subjects were assigned to NSA (n=51, blue squares) and SA (n=69, red triangles) cohorts by SARP criteria. (A) $LXA_4$ and (B) 15-epi-$LXA_4$ were extracted from BALF and quantitated by ELISA (see Methods). (C) ANXA1 and (D) SAA levels were determined by ELISA. Scatter plots show individual data points for each subject normalized to protein levels with the median value noted by the horizontal line (E) Flow cytometry was performed on viable BAL macrophages in n=32 HD, n=33 NSA, and n=38 SA subjects to measure surface ALX expression. Data are expressed as the ALX Index (MFI ALX divided by MFI isotype control). *$p<0.05$, $p<0.01$, *$p<0.005$, ****$p<0.001$ by Kruskal-Wallis test, followed by Dunn's test for multiple comparisons. BALF, bronchoalveolar lavage fluid; ALX, airway lipoxin $A_4$ receptor; HD, healthy donors; NSA, non-severe asthma; SA, severe asthma; SARP, severe asthma research program; $LXA_4$, lipoxin $A_4$; 15-epi-$LXA_4$, 15-epimer lipoxin $A_4$; ELISA, enzyme-linked immunosorbent assay; ANXA1, annexin A1; SAA, serum amyloid A; MFI, median fluorescence intensity.

In the study of patient health, inflammation resolution is known as an active process governed by specialized pro-resolving mediators and receptors. ALX/FPR2 receptors (ALX) are targeted by both pro-resolving and pro-inflammatory ligands for opposing signaling events, which suggest to Applicants pivotal roles for ALX in the fate of inflammatory responses.

In the Examples below, Applicants investigated whether ALX expression and ligands were linked to severe asthma (SA). ALX expression and levels of pro-resolving ligands (Lipoxin $A_4$ ($LXA_4$), 15-epi-$LXA_4$ and Annexin A1 (ANXA1)), and a pro-inflammatory ligand (Serum Amyloid A (SAA)) were measured in bronchoscopy samples collected in Severe Asthma Research Program-3 (SA (n=69), non-severe asthma (NSA, n=51) or healthy donors (HD, n=47)).

In brief, we found that bronchoalveolar lavage (BAL) fluid $LXA_4$ and 15-epi-$LXA_4$ were decreased and SAA was increased in SA relative to NSA (median SAA: 11.35 pg/μg protein in SA compared with 0 pg/μg protein in NSA). BAL macrophage ALX expression was increased in SA (BAL macrophage ALX index (MFI) ~5 in SA compared with ~3 in healthy donor). Subjects with LXA4low/SAAhigh levels had increased BAL neutrophils, more asthma symptoms, lower lung function, and increased relative risk for asthma exacerbation, sinusitis and gastroesophageal reflux disease and were assigned more frequently to SA clinical clusters. SAA and aliquots of LXA4low/SAAhigh BALF induced interleukin-8 production by lung epithelial cells expressing ALX receptors, which was inhibited by co-incubation with 15-epi-$LXA_4$.

Applicants conclude that these findings have established an association between select ALX receptor ligands and severity of chronic inflammatory diseases, such as asthma, that define a new biochemical endotype for inflammatory disease and support a pivotal functional role for ALX signaling in the fate of tissue inflammation.

Present Invention a. Diagnostic Method

In one embodiment, the present invention is a method of determining the severity of (and/or treatment for) a disease of chronic inflammation in a patient comprising: (1) collection or preparation of a bodily tissue, fluid, or lavage and (2) measurement of levels of ALX receptor ligands in the fluid, tissue, or lavage. The level of ALX receptor ligands or the ratio of the ligands predicts a clinical outcome or choice of treatment modality.

By "ALX receptor ligands" we mean to specifically include Lipoxin $A_4$ ($LXA_4$) and 15-epi-$LXA_4$ to levels of HD control or below to represent an inadequate counter-regulatory response to asthmatic inflammation and likely consistent with a diagnosis of SA relative to NSA.

Preferably, one would also measure the ALX receptor ligand serum amyloid A (SAA). In some patients, the levels of SAA increase with airway inflammation in SA. We would correlate an increase in BALF SAA to 1 pg/μg protein or more to be associated with SA. Examined together, the levels of lipoxin$A_4$ (low) and serum amyloid A (high) predict a severe disease clinical outcome, including more lung inflammation, more asthma symptomology, lower lung function and an increased risk for asthma co-morbidities.

For example, severe immunological diseases, such as severe asthma, would have at least a 3-fold and preferably at least a 5-fold or greater increase in the ratio (SAA/LXA4) relative to non-severe asthma. For more information regarding the ratio, one is directed to FIG. 5 in JCI Insight, 2017:2[4] e93534, Ricklefs, et al, ALX receptor ligands define a biochemical endotype for severe asthma, incorporated by reference herein.

Controls for the method of the present invention might be either milder/reversible forms of the same disease (as here with NSA) or potentially healthy subjects. Tissue would be a preferred standard for the measurements.

In one embodiment of the invention, the disease of chronic inflammation disease is lung inflammation and may be severe asthma (SA) or cystic fibrosis. In another embodiment, the lung inflammation is part of COPD, bronchiectasis, bronchiolitis, interstitial lung disease, transplant rejection, pneumonitis, lung abscess, pulmonary vascular disease, pulmonary emboli, or ARDS (acute respiratory distress syndrome).

In another embodiment of the invention, the chronic inflammation disease is selected from the group consisting of lung inflammation, arthritis, inflammatory bowel disease atherosclerosis and psoriasis.

If one were to diagnose a non-SA inflammatory disease, the biomarkers and ranges the expected to be similar if not the same. One would most preferably use afflicted tissue, which would be specific to each indication.

In the present invention, one must first examine patient tissue, fluid or lavage. In some embodiments of the invention, especially those involved with SA diagnosis, the fluid or lavage is bronchoalveolar lavage. In other embodiments, the tissue or fluid is selected from the group consisting of blood, serum, plasma, urine, nasal lavage, sputum, exhaled breath condensate, tears, breast milk, semen, pleural fluid, pericardial fluid, and joint fluid.

In another embodiment of the invention, one would use the information obtained above to determine a treatment regimen. An evaluation of the markers listed above would allow one to determine that the patient has an inflammatory disease, such as SA, and a pro-resolving mediator would be indicated.

Most important is that the pro-resolving mediator serve as a ligand for the $ALX/FPR_2$ receptor. 15-epi-$LXA_4$ is such a ligand. It serves as an allosteric inhibitor of the pro-inflammatory signaling serum amyloid A at the same receptor and also mediates pro-resolving actions via interactions with the same $ALX/FPR_2$ receptor. In addition to 15-epi-$LXA_4$, other pro-resolving ligands for $ALX/FPR_2$ include lipoxin $A_4$, lipoxin $A_4$ bioactive analogs and mimetics, 17-epi-resolvin D1, and resolvin D1 bioactive analogs and mimetics. For example, one may examine U.S. Pat. Nos. 7,906,678 and 6,831,186 for exemplary Lipoxin $A_4$ analogs. Other exemplary analogs are disclosed in U.S. Pat. No. 7,700,650, PCT/US02/06404, PCT/US02/35860, and PCT/US00/06582.

In another embodiment, one would examine tissue, fluid or lavage for the expression of the $ALX/FPR_2$ receptor by macrophages (in the tissue, fluid or lavage). An increase compared to control samples predicts a severe disease clinical outcome, including more lung inflammation, more asthma symptomology, lower lung function and an increased risk for asthma co-morbidities. The Example below discloses a preferred embodiment where the increase in receptor expression predicted SA.

In this embodiment of the invention, one would be evaluating the increase in the following manner: An increase of preferably at least 5 would indicate an increased likelihood of a diagnosis of SA rather than NSA.

a. Measurement of Biomarkers

In another embodiment, the present invention is a method of examining a patient tissue, fluid, or lavage and measuring or examining the levels of specific ALX receptor ligands, such as Lipoxin $A_4$ ($LXA_4$), 15-epi-$LXA_4$, and serum amyloid A (SAA). In one preferred embodiment, one would measure all three markers. In another embodiment, one would measure $LXA_4$ and 15-epi-$LXA_4$ or $LXA_4$ along with SAA. In a preferred version of the invention, one would measure the markers and determine the ratio of $LXA_4$ and SAA.

In some embodiments of the invention, especially those involved with SA diagnosis, the fluid or lavage is bronchoalveolar lavage. In other embodiments, the tissue or fluid is selected from the group consisting of blood, serum, plasma, urine, nasal lavage, sputum, exhaled breath condensate, tears, breast milk, semen, pleural fluid, pericardial fluid, and joint fluid.

The markers are typically measured by methods currently known in the art. For example, one might use the ELISA methods described below and in standard references. One could obtain useful antibodies at a custom research products organization, such as Cayman Chemical (Ann Arbor, Mich.). Other methods might include physical methods of detection such as lipidomics and proteomics.

EXAMPLES

Subject Characteristics

Subjects with SA and NSA, and non-asthmatic HD were recruited to participate in SARP-3 at seven research centers across the United States. Relative to NSA, subjects with SA had increased symptoms as manifested by lower Asthma Control Test (ACT) and higher Asthma Control Questionnaire (ACQ) scores. Spirometric measures of lung function were lower in SA than NSA and HD despite the SA cohort's use of more asthma-targeted medications (Table 1). A subset of subjects agreed to bronchoscopy with bronchoalveolar lavage (BAL) as part of their baseline phenotyping. SA subjects had more lung inflammation with increased BAL neutrophils (Table 1).

Severe asthma subjects have decreased lipoxins and increased SAA and macrophage ALX receptor expression.

The fate of innate inflammatory responses is dictated in part by ALX receptor signaling (16, 21), so the presence of BAL fluid (BALF) ALX ligands with pro-inflammatory (i.e., SAA) or pro-resolving properties (i.e., $LXA_4$, 15-epi-$LXA_4$ and ANXA1) and BAL cell surface ALX receptor expression were determined. SA subjects had significantly less BALF $LXA_4$ (median: 0.23 pg/µg protein, mean: 0.28 pg/µg protein) and 15-epi-$LXA_4$ (median: 1.02 pg/µg protein, mean: 1.24 pg/µg protein) than NSA subjects ($LXA_4$: median 0.32 pg/µg protein, mean 0.40 pg/µg protein; 15-epi-$LXA_4$: median 1.47 pg/µg protein, mean 1.88 pg/µg protein) (FIG. 1A-B). BALF lipoxins were significantly increased in NSA relative to HD, without significant differences between SA and HD cohorts (FIG. 1A-B), consistent with the findings in an earlier SARP cohort (14). No significant differences in immunoreactive ANXA1 levels were identified between the cohorts (FIG. 1C). In contrast, SAA levels were increased in SA (median: 3.03 pg/µg protein, mean 11.35 pg/µg protein) relative to NSA (median: 0 pg/µg protein, mean 11.21 pg/µg protein) (FIG. 1D). Of note, BALF SAA levels were below the limit of detection in 51 of the 120 asthma subjects and these samples were arbitrarily assigned a value of 0 pg/µg protein for analysis. Differences in BALF ALX ligand levels were also present when BALF was not corrected for protein. BAL macrophage surface ALX receptor expression was determined by flow cytometry with data expressed as a normalized index for ALX (MFI of ALX divided by MFI of isotype control) (see Methods). A step-wise increase in the BAL macrophage ALX index from HD to NSA to SA was detected (FIG. 1E).

ALX ligands differentially correlate with asthma inflammation, symptoms, and lung function.

Figure 2:
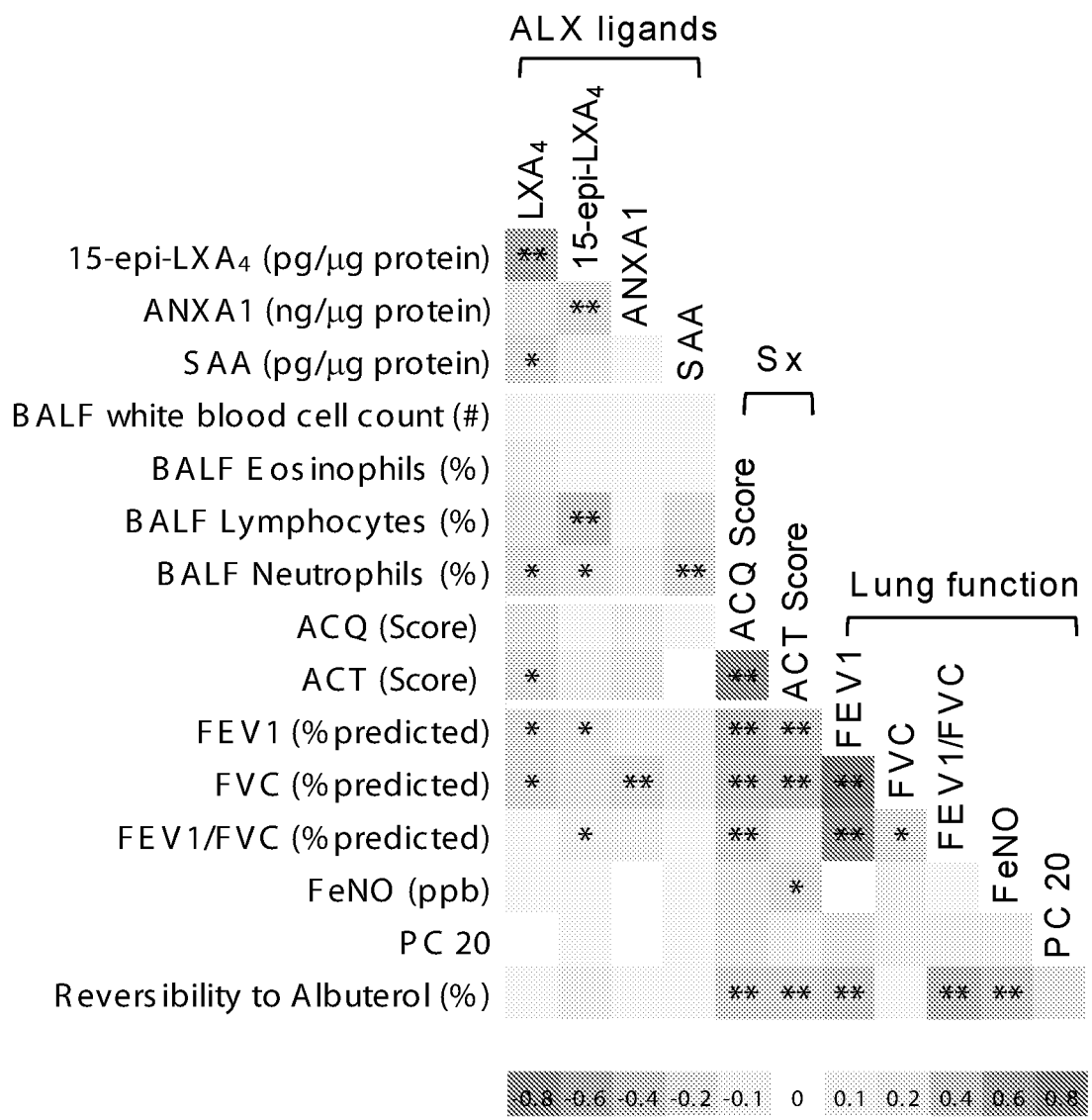
FIG. 2. Relationship between ALX ligands, lung inflammation, asthma symptoms and lung function in asthma. The relationships between BALF ALX ligand levels, BAL leukocytes, asthma symptom score, and measures of lung function, were determined by Pearson correlation matrix (see Methods) for n=51 NSA and n=69 SA subjects. Positive correlations are noted in blue and negative correlation in red. The color intensity is proportional to Pearson's correlation coefficient with deeper colors denoting stronger associations. *$p<0.05$, **$p<0.01$ by Pearson correlation analysis. BALF, bronchoalveolar lavage fluid; ALX, airway lipoxin $A_4$ receptor; NSA, non-severe asthma; SA, severe asthma; $LXA_4$, lipoxin $A_4$; 15-epi-$LXA_4$, 15-epimer lipoxin $A_4$; ANXA1, annexin A1; SAA, serum amyloid A; ACQ, asthma control questionnaire; ACT, asthma control test; FEV1, forced expiratory volume in 1 second; FVC, forced vital capacity; FeNO, fractional exhaled nitric oxide; PC 20, provocation challenge causing a 20% fall in FEV1.

To screen for relationships between the BALF ALX ligand levels and asthma clinical parameters, a Pearson correlation matrix was constructed using measures of disease activity from all asthma subjects (NSA and SA; n=120) (FIG. 2). $LXA_4$ levels correlated positively with 15-epi-$LXA_4$ and inversely with SAA. The ALX ligands were also compared to clinical parameters of lung inflammation, asthma symptoms and measures of lung function. Notably, the percentage of BALF neutrophils was inversely correlated with $LXA_4$ and 15-epi-$LXA_4$ and positively correlated with SAA. As expected, the ACQ and ACT scores were inversely correlated and significantly related to lung function. BALF levels of $LXA_4$ were inversely correlated with asthma symptoms (i.e., high ACQ, low ACT scores). $LXA_4$ and 15-epi-LXA$_4$ were also positively associated with lung function. SAA was not significantly related to asthma symptoms or lung function parameters. There were no significant correlations between BALF ALX ligand levels and FeNO, methacholine PC$_{20}$ or lung function reversibility with albuterol. Because of limited sample size, this analysis was not corrected for multiple comparison testing, yet it strongly suggested relationships between select ALX ligands and major characteristics of clinical asthma, namely lung inflammation, asthma symptoms, and lung function.

BAL neutrophilia in severe asthma is associated with decreased LXA$_4$ and increased SAA levels.

BAL leukocyte subsets were determined in NSA and SA subjects and HD. As expected, macrophages were the most numerous BAL cell type accounting for 88-92% of BAL leukocytes (FIG. 3A). SA subjects had significantly higher percentages of BAL neutrophils than NSA subjects (mean+/−SEM; 3.32+/−0.59% SA versus 1.38+/−0.19% NSA; FIG. 3B). There were also trends for increased BAL lymphocytes and eosinophils in SA relative to NSA and HD (FIG. 3C-D). BALF LXA$_4$ levels inversely correlated with BAL neutrophil percentage in the total asthma cohort or when the SA cohort was analyzed independently (FIG. 3E-F). In contrast, SAA levels were positively correlated with BAL neutrophil percentage in the complete asthma cohort as well as when SA was analyzed separately (FIG. 3G-H). LXA$_4$ levels were also positively correlated with lung function (i.e. FEV1 and FVC (% predicted values)), but there was no correlation between SAA levels and lung function in this cohort.

ALX receptor ligands and expression are associated with asthma symptoms.

To further investigate relationships between the ALX signaling pathway and measures of asthma symptoms, the continuous variables for BAL ALX ligands were converted to categorical high and low subgroups using the median value to define a cutoff between the subgroups. Using the median BALF SAA value (1.22 pg/µg protein; FIG. 4A), the relationships between "SAA$^{high}$," and "SAA$^{low}$" subjects and measures of asthma symptoms were determined. Subjects defined as SAA$^{high}$ had significantly increased ACQ and decreased ACT scores relative to SAA$^{low}$ subjects (FIG. 4B), consistent with increased asthma symptoms in the SAA$^{high}$ group. When stratified by asthma severity, there were more NSA subjects that were SAA$^{low}$ and more SA subjects that were SAA$^{high}$ (FIG. 4C). ACQ scores were significantly different between SAA$^{low}$ and SAA$^{high}$ subjects when considering only those subjects with SA (FIG. 4D). Of note, significant differences between the SAA$^{high}$ and SAA$^{low}$ cohorts for ACQ and ACT scores were not apparent in the NSA cohort.

Because BALF LXA$_4$ levels were inversely related to SAA levels and asthma symptoms by Pearson correlation (FIG. 2), the difference between LXA$_4$$^{high}$ and LXA$_4$$^{low}$ groups of subjects and asthma symptoms was determined. The median LXA$_4$ level was used as a cutoff between groups (0.23 pg/µg protein; FIG. 4E). LXA$_4$$^{low}$ subjects had higher ACQ scores and significantly lower ACT scores compared to LXA$_4$$^{high}$ subjects consistent with more symptoms in the LXA$_4$$^{low}$ group (FIG. 4F). When stratified by severity, NSA subjects were more numerous in the LXA$_4$$^{high}$ group and approximately 70% of the LXA$_4$$^{low}$ cohort were subjects with SA (FIG. 4G). In contrast to our findings with SAA, the low LXA$_4$ levels were not significantly related to symptom scores in the SA cohort (FIG. 4H); however, amongst NSA subjects, the LXA$_4$$^{high}$ group did have significantly fewer symptoms as evidenced by higher ACT scores (Supplemental FIG. 3B). Of note, administration of a single dose of intramuscular triamcinolone did not result in discernible changes in either LXA$_4$ or SAA levels after 3 to 6 weeks in either SA or NSA subjects.

With opposing relationships for asthma symptoms for the ALX ligands SAA and LXA$_4$, we next performed similar analyses for the BAL macrophage ALX index. Asthma subjects were categorized into ALX$^{high}$ and ALX$^{low}$ cohorts using the median ALX Index to define the cutoff between subgroups (median=4.61; FIG. 4I). ALX$^{high}$ asthma subjects had higher ACQ scores and significantly lower ACT scores, consistent with increased asthma symptoms (FIG. 4J). After stratification by asthma severity (FIG. 4K), ALX$^{high}$ subjects had significantly increased symptoms by both measures (i.e., ACQ and ACT) in the SA cohort (FIG. 4L). The ALX index was not significantly linked to symptom score in the NSA cohort (Supplemental FIG. 3C). Of added interest, the BAL macrophage ALX index correlated with macrophage indices of MHC class 2 and CD206 expression in asthma subjects.

SAA and LXA$_4$ levels together represent a biochemical endotype that distinguishes SA from NSA.

Individually, SAA and LXA$_4$ levels were both associated with asthma severity. More SA subjects had SAA$^{high}$ and LXA$_4$$^{low}$ levels and more NSA subjects had SAA$^{low}$ and LXA$_4$$^{high}$ levels (FIG. 4). In SA, macrophage ALX expression was increased (FIG. 1) and associated with increased asthma symptoms (FIG. 4), so we next determined if BALF levels for the combination of the ALX ligands was linked to SA. Asthma subjects were divided into 4 groups based on BALF LXA$_4$ and SAA levels (FIG. 5A). The approach of categorical grouping of high and low (based on median values) was chosen because the relationship between an individual's BALF LXA$_4$ and SAA levels suggested that these ALX ligands were independently regulated (FIG. 5A). When subjects were stratified by clinical severity, it was striking that more than half of NSA but fewer than a quarter of SA were LXA$_4$$^{high}$SAA$^{low}$ (beige, FIG. 5B). In contrast, 41% of SA subjects were LXA$_4$$^{low}$SAA$^{high}$ compared to 22% of NSA subjects (purple, FIG. 5B). Of note, for asthmatic subjects, the relative ratio of BALF SAA to LXA$_4$ levels was strongly correlated with BAL neutrophilia (FIG. 5C), more so than the level of either ALX ligand independently (FIGS. 3E and 3G). When comparing asthmatic subjects in these two distinct groups, the LXA$_4$$^{low}$SAA$^{high}$ group had significantly higher BAL neutrophils and asthma symptoms (i.e., higher ACQ, lower ACT) and lower lung function (i.e., % predicted FEV$_1$ and FVC) than the LXA$_4$$^{high}$SAA$^{low}$ group (FIG. 5D-F). The total BAL white blood count and percentage of lymphocytes and eosinophils did not differ between the two groups. The percent of subjects with an ACQ score >1.5 was higher in the LXA$_4$$^{low}$SAA$^{high}$ cohort, representing another measure of the increased symptoms in this group.

Cluster analyses from SARP-1 used clinical parameters to identify five asthma subtypes (mild allergic asthma, mild-moderate allergic asthma, more severe older onset asthma, severe variable allergic asthma, and severe fixed airflow asthma) (5). Using this classification here with SAA and LXA$_4$ as biochemical markers of ALX receptor signaling, it was notable that 71% of the LXA$_4$$^{high}$SAA$^{low}$ group were assigned to one of the NSA clusters and 64% of the LXA$_4$$^{low}$SAA$^{high}$ subjects were assigned to one of the SA clusters (FIG. 5G). FIG. 6E).

SAA is an acute phase protein and with the relationship for the LXA$_4$$^{low}$SAA$^{high}$ endotype to asthma severity and neutrophilic lung inflammation, we next determined if there was a relationship for LXA$_4$ and SAA to exacerbations and common asthma comorbidities. Both high SAA and low $LXA_4$ levels were significantly related to sinusitis, gastroesophageal reflux disease (GERD) and obesity (BMI>30) and low $LXA_4$ was also related to history of more frequent acute exacerbation over the prior year (Table 2). Together, the combination of low $LXA_4$ levels and high SAA levels (i.e. the $LXA_4^{low}SAA^{high}$ endotype) was even more closely associated with these asthma comorbidities (Table 2).

SAA and 15-epi-$LXA_4$ signaling via ALX receptors regulates production of the neutrophil chemoattractant IL-8.

To determine the functional relationship for these ALX receptor ligands, we next turned to an ALX-dependent in vitro reporter assay that we have previously qualified in chronic obstructive pulmonary disease (18). A549 lung epithelial cells were stably transfected to express the human ALX/FPR2 receptor (hALX). BALF samples were selected from HD, NSA, and SA subjects with representative levels of ALX ligands (FIG. 6A). SAA gave a concentration-dependent (0-10 ng/ml) increase in IL-8 production by $A549^{hALX}$ cells (FIG. 6B). When the $A549^{hALX}$ cells were exposed to BALF (see Methods), several of the representative SA BALFs substantially increased IL-8 production (FIG. 6C), reflective of the relative amounts of BALF SAA and $LXA_4$. The addition of exogenous 15-epi-$LXA_4$ inhibited $A549^{hALX}$ cell IL-8 production by cells conditioned with BALF (FIG. 6D). Of note, maximal inhibition of IL-8 production by 15-epi-$LXA_4$ was for $A549^{hALX}$ cells that had been conditioned with BALF from $LXA_4^{low}SAA^{high}$ subjects (FIG. 6D).

DISCUSSION

Here, in SARP-3, we measured the abundance of four ligands for ALX receptors, namely $LXA_4$, 15-epi-$LXA_4$, ANXA1 and SAA, with the potential for opposing effects on asthmatic airway responses. In SA, BAL macrophage ALX receptor expression was increased and BALF ligands for ALX were selectively regulated. BALF levels of pro-resolving lipoxins were decreased and levels of pro-inflammatory SAA were increased in SA. Levels of lipoxins inversely correlated to SAA, BAL neutrophils and asthma symptoms and lipoxins were positively correlated to measures of lung function. $SAA^{high}$ and $ALX^{high}$ subjects more commonly had SA with increased ACQ and decreased ACT scores. When $LXA_4$ and SAA levels were considered together in a combined endotype, a stronger association with asthma symptoms, lung function, and airway neutrophilia was noted than when either mediator was considered individually. $LXA_4^{low}SAA^{high}$ subjects had more lung inflammation and asthma symptoms and lower lung function relative to $LXA_4^{high}SAA^{low}$ subjects. $LXA_4^{low}SAA^{high}$ and $LXA_4^{high}SAA^{low}$ subjects segregated to SA and NSA clinical clusters, respectively. Importantly, $LXA_4^{low}SAA^{high}$ subjects had significantly increased likelihood for asthma exacerbation in the past year and for the asthma comorbidities of sinusitis, GERD and obesity. Exposure to SAA or BALF from SA subjects increased production of the neutrophil chemoattractant IL-8 by ALX-expressing human lung epithelial cells in vitro. This SAA-driven IL-8 production by epithelial cells was mitigated by exposure to 15-epi-$LXA_4$ at pharmacological doses, supporting a functional interaction between the ALX ligands relevant to the neutrophilic inflammation in SA. Together, these findings support a mechanistic role for ALX receptor signaling by SAA and $LXA_4$ in lung inflammation in SA that defines a new biochemical endotype for patient stratification in asthma.

ALX receptors are intriguing targets for regulating the fate of inflammatory responses. $LXA_4$ and SAA interact with ALX receptors to exert opposing effects on inflammation (18). ALX receptors are seven-membrane-spanning, G-protein coupled receptors that are present on several lung cell types relevant to asthma pathogenesis, including neutrophils (22), eosinophils (23), group 2 innate lymphoid cells (24), natural killer cells (24), lymphocytes (25), monocytes (26), dendritic cells (27, 28), macrophages (29) and airway structural cells (30). $LXA_4$ is a high affinity ligand for ALX that signals for anti-inflammatory and pro-resolving cellular responses (16). SAA binds with lower affinity, yet this acute phase reactant is substantially more abundant than $LXA_4$ during infection and the upstroke of acute inflammation (18). Also relevant in SA patients with comorbidities, corticosteroids can enhance SAA production, especially in conjunction with LPS (18). Distinct from $LXA_4$'s interaction with the seventh transmembrane domain and adjacent regions (31, 32), SAA interacts with the first and second extracellular loop domains (33), resulting in a marked shift in receptor conformation and dimerization that changes the receptor's pro-resolving signaling to pro-inflammatory signaling (17). Here in SA, ALX expression was increased on BAL macrophages and associated with increased asthma symptoms. Macrophage ALX expression correlated with surface CD206 expression, which marks "M2" macrophages that participate in endogenous pathways of inflammation resolution (34, 35). Together with the increased SAA and decreased lipoxins in SA BALF, the increase in ALX expression on BAL macrophages likely reflects SAA-driven outcomes, including the increased lung inflammation (i.e., BAL neutrophilia) despite higher doses of corticosteroids. With the presence of SAA and $LXA_4$ in proximity to ALX receptors in the lung and their divergent influences on inflammatory responses, ALX receptors are poised to serve as a pivotal signaling *nexus* for acute inflammation or its resolution.

Lipoxins are products of arachidonic acid metabolism that are structurally and functionally distinct from leukotrienes and prostaglandins. Lipoxin $A_4$ was first detected in humans in BALF from patients with lung disease, including asthma (36). Lipoxins are the lead members of a new genus of endogenous chemical signals termed specialized pro-resolving mediators (SPMs), which are partially defined by their ability to inhibit granulocyte recruitment and activation in inflamed tissues as well as to promote macrophage-mediated clearance of dead cells, microbes and debris in catabasis (8). Distinct from increased leukotriene production by some asthmatic patients, lipoxin levels are decreased in uncontrolled and severe asthma (13). Current anti-leukotriene drugs would not be expected to increase lipoxins in asthma. There are likely multiple factors responsible for the defective lipoxin production in severe asthma; however, the increased oxidative stress in SA airways was recently determined to be a major cause for reduced lipoxin generation (11). In human studies, inhaled $LXA_4$ dampens bronchoprovocation in asthma (10) and lipoxins regulate cytokine mediated increases in bronchial constriction to methacholine, histamine and thromboxane (11). Recently, a stable $LXA_4$ analog was shown to markedly decrease allergic inflammation and symptoms in patients with juvenile eczema (37). Preclinical studies have established that $LXA_4$ analogs that resist metabolic inactivation can prevent and potently reduce allergen-driven airway hyper-responsiveness to methacholine, airway mucus metaplasia and Type 2 inflammation (38, 39). Transgenic expression of hALX receptors also display decreased inflammatory responses to allergen, supporting a role for endogenous ALX ligands in anti-inflammation and pro-resolution (23). In addition to ALX, lipoxins can interact with additional receptors, including cysLT1—the pharmacological target of one of the classes of anti-leukotriene drugs (40). Together, these findings point to pivotal pro-resolving roles for lipoxins in health to control airway phlogistic responses and promote their resolution. Here, the diminished BALF levels of lipoxins in SA would be predicted from prior publications to disable a major endogenous regulatory pathway for airway inflammation, mucus and hyper-reactivity and our results show a strong and consistent correlation between low $LXA_4$ and increased lung inflammation, asthma symptoms and comorbidities, and lower lung function in SA.

In contrast to lipoxins, there are several peptide ligands for ALX receptors that engage these receptors to promote inflammatory responses. The acute phase reactant SAA is one of the ALX peptide ligands and can induce neutrophil chemotaxis and activation via ALX (41, 42). SAA is increased in severe allergic asthma (43) and can prevent dendritic cell apoptosis to induce glucocorticoid resistance for $CD4^+$ T cells (44). Here, BALF SAA levels were increased in SA and strongly associated with BAL neutrophils. $SAA^{high}$ subjects had increased asthma symptoms and a higher relative risk of sinusitis, GERD and obesity. If subjects had both low $LXA_4$ levels and high SAA levels (i.e., $LXA_4^{low}SAA^{high}$) then their relative risk for BAL neutrophils, asthma symptoms, and lower lung function were all increased. Recently, some subjects with SA with non-Type 2 inflammation were identified as $IL-6^{high}$ (45). IL-6 induces SAA expression (46) and may conspire with this acute phase protein to activate neutrophils and non-Type-2 lung inflammation in SA, in particular in those with systemic metabolic alterations associated with obesity. With $A549^{hALX}$ epithelial cells, BALF from $LXA_4^{low}SAA^{high}$ subjects increased production of the neutrophil chemoattractant IL-8, which was inhibitable by 15-epi-$LXA_4$. At ALX receptors, 15-epi-$LXA_4$ inhibition of SAA is allosteric in nature (18), and when given at pharmacological doses, 15-epi-$LXA_4$ can decrease SAA-driven IL-8 production by human airway epithelial cells in vitro and SAA-mediated acute inflammation in vivo in mice (18). Of interest for SA, SAA production is increased by corticosteroids and its expression is synergistically increased by the combination of steroids and LPS (18). Additional soluble mediators acting via distinct or synergistic pathways with SAA also are likely to contribute to epithelial cell IL-8 production and neutrophil chemoattraction in severe asthma. Subjects enrolled in SARP-3 were clinically characterized before and after intramuscular triamcinolone and adult subjects with SA continued to manifest lower $FEV_1$ and worse asthma control as compared to NSA after the systemic corticosteroids (47). Of note, BALF levels of $LXA_4$, 15-epi $LXA_4$, and SAA were not significantly altered by a single dose of intramuscular triamcinolone when measured 3 to 6 weeks after steroid administration. Unlike 15-epi-$LXA_4$, corticosteroids do not inhibit SAA-mediated lung inflammation (18), suggesting that for some subjects with SA their chronic neutrophilic lung inflammation could be perpetuated by corticosteroids and that SAA levels could inform more precise asthma management by helping to identify subjects at risk for this unintended consequence of corticosteroids.

Biochemical analyses here have linked ALX receptor signaling to the pathophysiology of SA. Using clinical and statistical approaches, five phenotypes of adult asthma have been defined (5), but there remains a need to connect these phenotypes to distinct molecular mechanisms for SA pathogenesis (6). We chose a candidate pathway approach based on preclinical evidence that linked ALX signaling to SA and BAL $LXA_4$ and SAA levels segregated subjects into discrete clinical clusters, suggesting that this biochemical pathway could convey additional value for patient stratification as an asthma endotype. Findings here suggest that these ALX ligands should be included in future studies designed to comprehensively model genetic, metabolic, and environmental influences and clinical characteristics for patient endotyping in SA.

Here, we have identified significant associations for BALF $LXA_4^{low}SAA^{high}$ levels with neutrophilic lung inflammation and poorly controlled asthma; however, there are several potential limitations to consider. While it was advantageous for biochemical analyses to have a relatively large number of BAL samples from this carefully phenotyped group of asthma subjects, it would not be practical to routinely perform bronchoscopy in a clinical (or clinical trial) setting. It will be important in future studies to obtain and analyze respiratory samples collected by less invasive means (i.e., sputum, exhaled breath condensate) to determine the influence of anatomic compartment on the relationships uncovered here with bronchoscopy specimens. The cross-sectional nature of the analyses here does not address the stability of this endotype, a question best addressed with samples obtained by less invasive means. Regarding additional ALX ligands, the ELISA used here for ANXA1 does not distinguish between intact and cleaved protein, so the absence of a relationship here does not preclude its potential existence when more specific experimental tools become available. There are also several additional peptide and lipid ligands for ALX receptors that might further enhance the discriminatory power of ALX signaling for identification of asthma endotypes.

In summary, ALX receptor expression was increased in asthmatic BAL macrophages and we have identified a cassette of ALX receptor ligands that are selectively regulated in BALF in asthma. Levels of lipoxins and SAA correlated with lung inflammation and clinical parameters of asthma control. In particular, subjects with $LXA_4^{low}SAA^{high}$ BALF were more likely to have SA with increased BAL neutrophils, asthma symptoms and asthma comorbidities and decreased lung function. At pharmacological levels, 15-epi-$LXA_4$ functionally opposed SAA signaling at ALX receptors to inhibit production of the neutrophil chemoattractant IL-8. BALF $LXA_4^{low}SAA^{high}$ subjects were assigned to discrete clinical clusters from $LXA_4^{high}SAA^{low}$ subjects, suggesting that these biochemical mediators could identify subgroups of asthma subjects and serve as a new asthma biochemical endotype for non-Type 2, steroid resistant inflammation in SA.

Materials and Methods

Study Design

SARP-3 is an NHLBI-funded study designed to characterize molecular, cellular and physiological phenotypes in subjects with SA and NSA (NCT01606826). Asthmatic and healthy subjects were recruited and completed baseline characterization with some subjects agreeing to bronchoscopy. Details regarding SARP methods, subject enrollment, and study procedures can be found in reference (45).

Participants and Sample Collection

Subjects 13 years of age and older with asthma and healthy control subjects were recruited between November 2012 and February 2015 by seven geographically dispersed, research centers in the USA. European Respiratory Society/American Thoracic Society guidelines were used to categorize subjects as SA or NSA (48). Control subjects were individuals who reported general health and were non-smokers with no history of lung disease, atopic disease or allergic rhinitis. BAL was performed with three 50 mL aliquots of warm saline, and BALF were recovered by hand suction. Subjects received intramuscular triamcinolone (1 mg/kg up to a maximum dose of 40 mg) and some subjects agreed to undergo a second bronchoscopy 3 to 6 weeks later and BAL samples were collected in the same manner. BAL cells were enumerated and differential leukocyte counts determined. Cell-free BALF supernatant was divided into several aliquots. One aliquot of BALF (1 ml) was directly mixed with iced methanol (2 ml, for 1:2, vol/vol) before storing at −80° C. The other aliquots were directly stored at −80° C. The stored aliquots were later shipped to Brigham and Women's Hospital for analyses.

Lipid Extraction

Aliquots of BALF with methanol (1:2, vol:vol) were brought to dryness in vacuo using a BÜCHI Rotavapor R-200/205. The samples were resuspended with methanol (500 µl) and distilled/deionized water (10 ml) followed by extraction using C18 SepPak cartidges (Waters, Milford, Mass.) as in (13). The methyl formate fraction was brought to dryness under a gentle stream of nitrogen and each sample was resuspended in 1 ml of methanol and stored at −80° C. until $LXA_4$ and 15-epi-$LXA_4$ ELISAs were performed.

Protein Assay

Pierce BCA Protein Assay Kit (Thermo Fisher) was used for BALF protein determination. Samples with less than 25 µg of protein were excluded from further analysis (n=3; 1 NSA, 2 SA).

ELISA $LXA_4$ and 15-epi-$LXA_4$ levels in the BALF were measured by ELISA (Neogen, Lexington, Ky.). Extracted BALF samples stored in methanol were brought to dryness under a gentle stream of nitrogen and resuspended in ELISA buffer. SAA and ANXA1 levels were measured by ELISA in aliquots of BALF stored in the absence of methanol (SAA: Abazyme, Needham, Mass.; ANXA1: Cloud-Clone, Houston, Tex.). $LXA_4$, 15-epi-$LXA_4$, SAA and ANXA1 levels were normalized to the total protein content of the BALF. Some subjects had an SAA level below the limit of detection and these samples were assigned a value of 0 pg/µg protein for analysis. The median value for $LXA_4$ and SAA were used to segregate subjects into "high" and "low" subgroups.

Flow Cytometry

BAL cell pellets were available from a subgroup of subjects. For ex vivo staining, BALF cells were blocked with mouse serum (Sigma, St. Louis, Mo.) in PBS for 30 minutes at 4° C. The cells were then incubated with Viability Dye eFluorR660 (eBioscience, San Diego, Calif.) as per manufacturer's instructions followed by 30 minutes of incubation with the following antibodies to human proteins: anti-ALX (clone 304405, R&D Systems, Minneapolis, Minn.)-PerCP, anti-HLA-DR (major histocompatibility complex class II, L243)-allophycocyanin-Cy7 (APC-Cy7) (BD Biosciences, San Jose, Calif.) and anti-CD206 (macrophage mannose receptor, 19.2)-phycoerythrin (PE) (eBioscience) or with directly conjugated unrelated antibodies of the same isotype (BD Biosciences) at 4° C. Data were acquired on a Canto II flow cytometer (Becton Dickinson) and analyzed using FlowJo software version 10.1 (TreeStar, Ashland, Oreg.). Macrophages were identified as single cells (by doublet exclusion), viable (Viability Dye eFluorR660 negative), $CD206^+$ cells. The MFI of ALX, MHC class II and CD206 was assessed on macrophages and normalized with the MFI of the isotype control antibody (MFI cell surface marker/MFI isotype control=MFI index).

In Vitro A549 Cell Culture

A549 transfected to stably express the human ALX receptor were used (as in (18)). $A549^{hALX}$ cells were seeded into a 48-well plate ($5 \times 10^4$ cells/well) and cultured in RPMI 1640 (Lonza) supplemented with 2 mM L-glutamine, 10% heat-inactivated fetal calf serum (Gibco), penicillin (100 IU/mL) and streptomycin (100 µg/mL) at 37° C. in 5% $CO_2$ until confluent. When confluent, $A549^{hALX}$ cells were cultured with serum free media for 16 hours and then exposed to BALF (100 µl) and serum-free RPMI media (1001 µl, 1:1 vol:vol) for 24 hours (37° C., 5% $CO_2$). In select experiments, recombinant human SAA (0-10 ng/ml, Peprotech), 15-epi-$LXA_4$ (100 nM, Cayman Chemical) or vehicle control was added. At the end of the incubations, supernatants were collected on ice and stored at −80° C. IL-8 levels in the supernatants were measured by ELISA (R&D). If there was no increase in IL-8 production after exposure to BALF, the samples were assigned a value of zero (FIG. 6C).

Statistical Analysis

In figures, data are expressed either individually with indication of the median value or as mean±SEM; in tables, data are expressed as mean±SD. For violin plots in FIG. 4, bin sizes and widths were determined for each variable automatically in SPSS based on the underlying data distribution. Statistical significance of differences was assessed by two-tailed Student's t test, one-way ANOVA, Kruskal-Wallis test (when normality assumptions were not met), or chi-square test as noted using SPSS version 23.0 (IBM). Post hoc Tukey's test (for ANOVA analyses) and Dunn's test (for Kruskal-Wallis analyses) were used to correct for multiple comparisons. Correlations were evaluated by Pearson's correlation coefficient (r) and linear or non-linear (for graphs with log axes) regression lines are shown. Correlation analyses included samples with a value of 0 for statistical analysis, but data points with value of 0 were excluded for regression line analyses of detectable ALX ligands. A p-value of <0.05 was considered significant and the reported p values were adjusted for multiple comparisons.

TABLE 1

Clinical characteristics and bronchoalveolar lavage leukocytes for subjects undergoing bronchoscopy[#]

|  | Healthy Donors (HD) | Non-Severe Asthma (NSA) | Severe Asthma (SA) | NSA vs SA | HD vs. NSA | HD vs. SA |
|---|---|---|---|---|---|---|
| No. of subjects | 47 | 51 | 69 |  |  |  |
| Clinical data |  |  |  |  |  |  |
| Age | 40.1 ± 12.9 (20-62) | 36.9 ± 12.4 (18-61) | 42.4 ± 13.6 (14-67) | ns | ns | ns |
| % Male | 19 (40%) | 17 (33%) | 24 (35%) | ns | ns | ns |
| % African American | 11 (23%) | 14 (27%) | 22 (32%) | ns | ns | ns |
| % White | 31 (66%) | 37 (74%) | 45 (65%) | ns | ns | ns |
| BMI | 27.6 ± 5.7 (20-44) | 30.0 ± 9.2 (18-61) | 31.4 ± 8.2 (19-67) | ns | ns | * |

TABLE 1-continued

Clinical characteristics and bronchoalveolar lavage leukocytes for subjects undergoing bronchoscopy[#]

| | Healthy Donors (HD) | Non-Severe Asthma (NSA) | Severe Asthma (SA) | NSA vs SA | HD vs. NSA | HD vs. SA |
|---|---|---|---|---|---|---|
| Symptom control | | | | | | |
| % Uncontrolled[§] | n.a. | 32 (63%) | 68 (98%) | **** | | |
| ACQ | n.a. | 1.08 ± 0.9 (0-3) | 1.93 ± 1.1 (0-5) | **** | | |
| ACT | n.a. | 19.61 ± 34.0 (7-25) | 14.48 ± 4.5 (5-23) | **** | | |
| Lung function | | | | | | |
| FEV1 % predicted | 102.4 ± 12.5 (78.46-139.2) | 89.8 ± 16.3 (42-124) | 75.0 ± 19.1 (35-116) | **** | *** | **** |
| FVC % predicted | 104.7 ± 14.2 (84.12-137.2) | 102.6 ± 17.2 (64-145) | 89.4 ± 17.6 (52-133) | **** | ns | **** |
| FEV1/FVC | 97.7 ± 5.6 (85.4-109.6) | 87.5 ± 9.0 (61-109) | 82.8 ± 9.0 (62-106) | * | **** | **** |
| Medications | | | | | | |
| Inhaled corticosteroids | 0 (0%) | 35 (69%) | 67 (97%) | **** | | |
| High dose of inhaled corticosteroids | 0 (0%) | 4 (8%) | 66 (96%) | **** | | |
| Oral steroids | 0 (0%) | 0 (0%) | 16 (23%) | **** | | |
| Long acting beta agonists | 0 (0%) | 21 (37%) | 64 (93%) | **** | | |
| Long acting anticholinergic medication | 0 (0%) | 0 (0%) | 3 (4%) | $p = 0.13$ | | |
| Leukotriene receptor antagonists | 0 (0%) | 11 (22%) | 24 (35%) | $p = 0.12$ | | |
| Omalizumab | 0 (0%) | 1 (2%) | 8 (13%) | * | | |
| BAL leukocyte differentials | | | | | | |
| Total cell count (millions) | 4.9 ± 4.6 (0-25) | 4.0 ± 2.7 (0-12) | 6.4 ± 13.2 (0-107) | ns | ns | ns |
| Macrophages (%) | 91.7 ± 5.8 (73-99) | 92.2 ± 5.1 (79-99) | 87.7 ± 10.1 (53-99) | ** | ns | * |
| Neutrophils (%) | 1.6 ± 1.9 (0-10) | 1.4 ± 1.4 (0-7) | 3.3 ± 4.9 (0-24) | ** | ns | * |
| Eosinophils (%) | 0.3 ± 0.4 (0-2) | 1.1 ± 2.8 (0-17) | 1.8 ± 5.0 (0-35) | ns | ns | ns |
| Lymphocytes (%) | 6.5 ± 5.0 (0-22) | 5.3 ± 4.5 (0-19) | 7.3 ± 5.9 (0-34) | ns | ns | ns |

[#]Values represent the mean ± SD (range).
[§]Uncontrolled symptoms were defined as the occurrence of one of the following: ≥2 steroid bursts, hospitalization, intensive care unit admission, use of a ventilator, FEV1% predicted < 80%, ACT < 20, or self reported worsening with tapering steroids.
Definition of abbreviations: BMI = body mass index, ACQ = asthma control questionnaire, ACT = asthma control test, FEV1 = forced expiratory volume in one second, FVC = forced vital capacity,
n.a. = not applicable
*$P < 0.05$,
**$P < 0.01$,
****$P < 0.001$,
ns = not significant.
Comparison between three groups was performed by One-way-ANOVA followed by Tukey-test to adjust for multiple comparisons and Chi-squared test.
Comparison between two groups was performed by Student's t-test.

TABLE 2

Asthma exacerbations and comorbidities are associated with high SAA and low $LXA_4$.[#]

| | SAA low (n = 60) | SAA high (n = 60) | p-value (Chi-Squared) | p-value (Chi-Squared with Bonferroni correction) |
|---|---|---|---|---|
| >1 AE | 21 (35%) | 24 (40%) | n.s. | n.s. |
| Sinusitis | 12 (20%) | 24 (40%) | 0.01 | 0.04 |
| GERD | 18 (30%) | 28 (47%) | 0.04 | n.s. |
| BMI > 30 | 19 (32%) | 32 (53%) | 0.01 | 0.04 |

| | $LXA_4$ low (n = 60) | $LXA_4$ high (n = 60) | | |
|---|---|---|---|---|
| >1 AE | 29 (48%) | 16 (27%) | 0.01 | 0.04 |
| Sinusitis | 24 (40%) | 12 (20%) | 0.02 | n.s. |
| GERD | 29 (48%) | 17 (28%) | 0.01 | 0.04 |
| BMI > 30 | 34 (57%) | 17 (28%) | 0.002 | 0.008 |

| | SAA low $LXA_4$ high (n = 40) | SAA high $LXA_4$ low (n = 39) | | |
|---|---|---|---|---|
| >1 AE | 10 (25%) | 18 (46%) | <0.05 | n.s. |
| Sinusitis | 6 (15%) | 18 (46%) | 0.003 | 0.01 |
| GERD | 11 (28%) | 22 (56%) | 0.009 | 0.04 |
| BMI > 30 | 11 (41%) | 26 (74%) | <0.001 | <0.005 |

[#]Results are expressed as number of patients (percentage).
Definition of abbreviations: AE = acute exacerbation, GERD = gastroesophageal reflux, BMI = body mass index; n.s. = not significant.

REFERENCES

1. National Current Asthma Prevalence (2014). https://www.cdc.gov/asthma/most recent data.htm.
2. Levy B D, Noel P J, Freemer M M, Cloutier M M, Georas S N, Jarjour N N, et al. Future Research Directions in Asthma. An NHLBI Working Group Report. *Am J Respir Crit Care Med.* 2015; 192(11):1366-72.
3. Ray A, Raundhal M, Oriss T B, Ray P, and Wenzel S E. Current concepts of severe asthma. *The Journal of clinical investigation.* 2016; 126(7):2394-403.
4. Modena B D, Bleecker E R, Busse W W, Erzurum S C, Gaston B M, Jarjour N N, et al. Gene Expression Correlated to Severe Asthma Characteristics Reveals Heterogeneous Mechanisms of Severe Disease. *American journal of respiratory and critical care medicine.* 2016.
5. Moore W C, Meyers D A, Wenzel S E, Teague W G, Li H, Li X, et al. Identification of asthma phenotypes using cluster analysis in the Severe Asthma Research Program. *Am J Respir Crit Care Med.* 2010; 181(4):315-23.
6. Wenzel S E. Asthma phenotypes: the evolution from clinical to molecular approaches. *Nat Med.* 2012; 18(5):716-25.
7. Fahy J V. Type 2 inflammation in asthma—present in most, absent in many. *Nat Rev Immunol.* 2015; 15(1):57-65.
8. Serhan C N. Pro-resolving lipid mediators are leads for resolution physiology. *Nature.* 2014; 510(7503):92-101.
9. Levy B D, and Serhan C N. Resolution of acute inflammation in the lung. *Annual review of physiology.* 2014; 76:467-92.
10. Christie P E, Spur B W, and Lee T H. The effects of lipoxin A4 on airway responses in asthmatic subjects. *Am Rev Respir Dis.* 1992; 145(6):1281-4.
11. Ono E, Dutile S, Kazani S, Wechsler M E, Yang J, Hammock B D, et al. Lipoxin generation is related to soluble epoxide hydrolase activity in severe asthma. *American journal of respiratory and critical care medicine.* 2014; 190(8):886-97.
12. Kazani S, Planaguma A, Ono E, Bonini M, Zahid M, Marigowda G, et al. Exhaled breath condensate eicosanoid levels associate with asthma and its severity. *J Allergy Clin Immunol.* 2013; 132(3):547-53.
13. Levy B D, Bonnans C, Silverman E S, Palmer L J, Marigowda G, Israel E, et al. Diminished lipoxin biosynthesis in severe asthma. *Am J Respir Crit Care Med.* 2005; 172(7):824-30.
14. Planaguma A, Kazani S, Marigowda G, Haworth O, Mariani T J, Israel E, et al. Airway lipoxin A4 generation and lipoxin A4 receptor expression are decreased in severe asthma. *Am J Respir Crit Care Med.* 2008; 178(6):574-82.
15. Vachier I, Bonnans C, Chavis C, Farce M, Godard P, Bousquet J, et al. Severe asthma is associated with a loss of LX4, an endogenous anti-inflammatory compound. *The Journal of allergy and clinical immunology.* 2005; 115(1):55-60.
16. Chiang N, Serhan C N, Dahlen S E, Drazen J M, Hay D W, Rovati G E, et al. The lipoxin receptor ALX: potent ligand-specific and stereoselective actions in vivo. *Pharmacological reviews.* 2006; 58(3):463-87.
17. Cooray S N, Gobbetti T, Montero-Melendez T, McArthur S, Thompson D, Clark A J, et al. Ligand-specific conformational change of the G-protein-coupled receptor ALX/FPR2 determines proresolving functional responses. *Proc Natl Acad Sci USA.* 2013; 110(45):18232-7.
18. Bozinovski S, Uddin M, Vlahos R, Thompson M, McQualter J L, Merritt A S, et al. Serum amyloid A opposes lipoxin A(4) to mediate glucocorticoid refractory lung inflammation in chronic obstructive pulmonary disease. *Proceedings of the National Academy of Sciences of the United States of America.* 2012; 109(3):935-40fff.
19. He R, Sang H, and Ye R D. Serum amyloid A induces IL-8 secretion through a G protein-coupled receptor, FPRL1/LXA4R. *Blood.* 2003; 101(4):1572-81.
20. Perretti M, Chiang N, La M, Fierro I M, Marullo S, Getting S J, et al. Endogenous lipid- and peptide-derived anti-inflammatory pathways generated with glucocorticoid and aspirin treatment activate the lipoxin A4 receptor. *Nature medicine.* 2002; 8(11):1296-302.
21. Morris T, Stables M, Colville-Nash P, Newson J, Bellingan G, de Souza P M, et al. Dichotomy in duration and severity of acute inflammatory responses in humans arising from differentially expressed proresolution pathways. *Proceedings of the National Academy of Sciences of the United States of America.* 2010; 107(19):8842-7.
22. Fiore S, Maddox J F, Perez H D, and Serhan C N. Identification of a human cDNA encoding a functional high affinity lipoxin A4 receptor. *The Journal of experimental medicine.* 1994; 180(1):253-60.
23. Levy B D, De Sanctis G T, Devchand P R, Kim E, Ackerman K, Schmidt B A, et al. Multi-pronged inhibition of airway hyper-responsiveness and inflammation by lipoxin A(4). *Nat Med.* 2002; 8(9):1018-23.
24. Barnig C, Cernadas M, Dutile S, Liu X, Perrella M A, Kazani S, et al. Lipoxin A4 regulates natural killer cell and type 2 innate lymphoid cell activation in asthma. *Sci Transl Med.* 2013; 5(174):174ra26.
25. Ariel A, Chiang N, Arita M, Petasis N A, and Serhan C N. Aspirin-triggered lipoxin A4 and B4 analogs block extracellular signal-regulated kinase-dependent TNF-alpha secretion from human T cells. *J Immunol.* 2003; 170(12):6266-72.
26. Romano M, Maddox J F, and Serhan C N. Activation of human monocytes and the acute monocytic leukemia cell line (THP-1) by lipoxins involves unique signaling pathways for lipoxin A4 versus lipoxin B4: evidence for differential Ca2+ mobilization. *J Immunol.* 1996; 157(5):2149-54.
27. Aliberti J, Hieny S, Reis e Sousa C, Serhan C N, and Sher A. Lipoxin-mediated inhibition of IL-12 production by DCs: a mechanism for regulation of microbial immunity. *Nature immunology.* 2002; 3(1):76-82.
28. Yang D, Chen Q, Le Y, Wang J M, and Oppenheim J J. Differential regulation of formyl peptide receptor-like 1 expression during the differentiation of monocytes to dendritic cells and macrophages. *J Immunol.* 2001; 166(6):4092-8.
29. Maderna P, Cottell D C, Toivonen T, Dufton N, Dalli J, Perretti M, et al. FPR2/ALX receptor expression and internalization are critical for lipoxin A4 and annexin-derived peptide-stimulated phagocytosis. *FASEB journal: official publication of the Federation of American Societies for Experimental Biology.* 2010; 24(11):4240-9.
30. Bonnans C, Fukunaga K, Levy M A, and Levy B D. Lipoxin A(4) regulates bronchial epithelial cell responses to acid injury. *The American journal of pathology.* 2006; 168(4):1064-72.
31. Chiang N, Fierro I M, Gronert K, and Serhan C N. Activation of lipoxin A(4) receptors by aspirin-triggered lipoxins and select peptides evokes ligand-specific responses in inflammation. *The Journal of experimental medicine.* 2000; 191(7):1197-208.

32. Chiang N, Gronert K, Clish C B, O'Brien J A, Freeman M W, and Serhan C N. Leukotriene B4 receptor transgenic mice reveal novel protective roles for lipoxins and aspirin-triggered lipoxins in reperfusion. *The Journal of clinical investigation.* 1999; 104(3):309-16.

33. Bena S, Brancaleone V, Wang J M, Perretti M, and Flower R J. Annexin A1 interaction with the FPR2/ALX receptor: identification of distinct domains and downstream associated signaling. *The Journal of biological chemistry.* 2012; 287(29):24690-7.

34. Chiang N, Dalli J, Colas R A, and Serhan C N. Identification of resolvin D2 receptor mediating resolution of infections and organ protection. *The Journal of experimental medicine.* 2015; 212(8):1203-17.

35. Dakin S G, Martinez F O, Yapp C, Wells G, Oppermann U, Dean B J, et al. Inflammation activation and resolution in human tendon disease. *Science translational medicine.* 2015; 7(311):311ra173.

36. Lee T H, Crea A E, Gant V, Spur B W, Marron B E, Nicolaou K C, et al. Identification of lipoxin A4 and its relationship to the sulfidopeptide leukotrienes C4, D4, and E4 in the bronchoalveolar lavage fluids obtained from patients with selected pulmonary diseases. *The American review of respiratory disease.* 1990; 141(6):1453-8.

37. Wu S H, Chen X Q, Liu B, Wu H J, and Dong L. Efficacy and safety of 15(R/S)-methyl-lipoxin A(4) in topical treatment of infantile eczema. *Br J Dermatol.* 2013; 168(1):172-8.

38. Haworth O, Cernadas M, Yang R, Serhan C N, and Levy B D. Resolvin E1 regulates interleukin 23, interferon-gamma and lipoxin A4 to promote the resolution of allergic airway inflammation. *Nat Immunol.* 2008; 9(8): 873-9.

39. Levy B D, Lukacs N W, Berlin A A, Schmidt B, Guilford W J, Serhan C N, et al. Lipoxin A4 stable analogs reduce allergic airway responses via mechanisms distinct from CysLT1 receptor antagonism. *FASEB journal: official publication of the Federation of American Societies for Experimental Biology.* 2007; 21(14):3877-84.

40. Gronert K, Martinsson-Niskanen T, Ravasi S, Chiang N, and Serhan C N. Selectivity of recombinant human leukotriene D(4), leukotriene B(4), and lipoxin A(4) receptors with aspirin-triggered 15-epi-LXA(4) and regulation of vascular and inflammatory responses. *The American journal of pathology.* 2001; 158(1):3-9.

41. Su S B, Gong W, Gao J L, Shen W, Murphy P M, Oppenheim J J, et al. A seven-transmembrane, G protein-coupled receptor, FPRL1, mediates the chemotactic activity of serum amyloid A for human phagocytic cells. *The Journal of experimental medicine.* 1999; 189(2):395-402.

42. El Kebir D, Jozsef L, Khreiss T, Pan W, Petasis N A, Serhan C N, et al. Aspirin-triggered lipoxins override the apoptosis-delaying action of serum amyloid A in human neutrophils: a novel mechanism for resolution of inflammation. *J Immunol.* 2007; 179(1):616-22.

43. Buyukozturk S, Gelincik A A, Genc S, Kocak H, Oneriyidogan Y, Erden S, et al. Acute phase reactants in allergic airway disease. *The Tohoku journal of experimental medicine.* 2004; 204(3):209-13.

44. Ather J L, Fortner K A, Budd R C, Anathy V, and Poynter M E. Serum amyloid A inhibits dendritic cell apoptosis to induce glucocorticoid resistance in CD4(+) T cells. *Cell death &disease.* 2013; 4:e786.

45. Peters M C, McGrath K W, Hawkins G A, Hastie A T, Levy B D, Israel E, et al. Plasma interleukin-6 concentrations, metabolic dysfunction, and asthma severity: a cross-sectional analysis of two cohorts. *Lancet Respir Med.* 2016; 4(7):574-84.

46. Hagihara K, Nishikawa T, Sugamata Y, Song J, Isobe T, Taga T, et al. Essential role of STAT3 in cytokine-driven NF-kappaB-mediated serum amyloid A gene expression. *Genes to cells: devoted to molecular & cellular mechanisms.* 2005; 10(11):1051-63.

47. Phipatanakul W, Mauger D T, Sorkness R L, Gaffin J M, Holguin F, Woodruff P G, et al. Effects of Age and Disease Severity on Systemic Corticosteroid Responses in Asthma. *Am J Respir Crit Care Med.* 2016.

48. Chung K F, Wenzel S E, Brozek J L, Bush A, Castro M, Sterk P J, et al. International ERS/ATS guidelines on definition, evaluation and treatment of severe asthma. *Eur Respir J.* 2014; 43(2):343-73.

We claim:

1. A method of mitigating or inhibiting asthma in a patient in need thereof comprising:
   (a) measuring ALX/FPR2 receptor expression and optionally ligands serum amyloid A (SAA) and lipoxin A4 (LXA4), and analogs or mimetics thereof in a fluid, tissue, or lavage;
   (b) comparing the expression of ALX/FPR2 to healthy control; and
   (c) administering LXA4 or analogs thereof in patients having elevated ALX/FPR2 and asthma.

2. The method of claim 1, wherein the fluid, tissue, or lavage is broncholalveolar lavage.

3. The method of claim 2 wherein the measurement is of at least one of ALX/FPR2, $LXA_4$, 15-epi-$LXA_4$ and SAA.

4. The method of claim 2 wherein the $LXA_4$, analogs comprise 15-epi-$LXA_4$, lipoxin A4 bioactive analogs and mimetics, 17-epi-resolvin D1, and resolvin D1 and resolvin D1 bioactive analogs and mimetics.

5. The method of claim 1 wherein the measurement is monitored over a course of treatment.

* * * * *